(12) United States Patent
Phuah et al.

(10) Patent No.: US 8,794,236 B2
(45) Date of Patent: Aug. 5, 2014

(54) CARDIAC MONITORING AND THERAPY USING A DEVICE FOR PROVIDING PRESSURE TREATMENT OF SLEEP DISORDERED BREATHING

(75) Inventors: Chee Keong Phuah, Sydney (AU); Steven Paul Farrugia, Lugarno (AU); Dion Charles Chewe Martin, Concord (AU); Christine Wei Chih Chan, Strathfield (AU)

(73) Assignee: ResMed Limited (AU)

( * ) Notice: Subject to any disclaimer, the term of this patent is extended or adjusted under 35 U.S.C. 154(b) by 1915 days.

(21) Appl. No.: 10/598,255

(22) PCT Filed: Feb. 24, 2005

(86) PCT No.: PCT/AU2005/000248
§ 371 (c)(1),
(2), (4) Date: Apr. 20, 2007

(87) PCT Pub. No.: WO2005/079897
PCT Pub. Date: Sep. 1, 2005

(65) Prior Publication Data
US 2008/0045813 A1 Feb. 21, 2008

Related U.S. Application Data

(60) Provisional application No. 60/547,812, filed on Feb. 25, 2004.

(51) Int. Cl.
*A61B 5/00* (2006.01)
*A61B 5/08* (2006.01)
*A61B 7/04* (2006.01)

(52) U.S. Cl.
USPC .............. 128/204.26; 128/204.18; 600/301; 600/532

(58) Field of Classification Search
None
See application file for complete search history.

(56) References Cited

U.S. PATENT DOCUMENTS

| | | | |
|---|---|---|---|
| 3,923,055 | A | 12/1975 | Hammacher |
| 4,155,356 | A | 5/1979 | Venegas |
| 5,704,345 | A | 1/1998 | Berthon-Jones |
| 5,794,615 | A | 8/1998 | Estes |
| 5,803,066 | A | 9/1998 | Rapoport et al. |
| 6,029,665 | A | 2/2000 | Berthon-Jones |

(Continued)

FOREIGN PATENT DOCUMENTS

WO 02/26283 4/2002

OTHER PUBLICATIONS

Berry et al. 2002 "The use of auto-titrating continuous positive airway pressure for treatment of adult obstructive sleep apnea" sleep 25(2):148-173.*

(Continued)

*Primary Examiner* — Jeffrey Stucker
*Assistant Examiner* — Adam M Weidner
(74) *Attorney, Agent, or Firm* — Lerner, David, Littenberg, Krumholz & Mentlik LLP

(57) ABSTRACT

A method of using CPAP equipment to sense cardiogenic oscillations in a patient's airflow, and to monitor and treat the patient's cardiac condition. The apparatus diagnoses cardiac morbidity conditions, such as the existence of arrhythmias or other cardiac abnormalities, and influences and optimizes cardiac stroke volume. The apparatus further monitors pulse-transit time, changes in the heart pre-ejection period, and the duration of the cardiac cycle.

51 Claims, 2 Drawing Sheets

(56) References Cited

U.S. PATENT DOCUMENTS

| | | | |
|---|---|---|---|
| 6,138,675 A * | 10/2000 | Berthon-Jones | 128/204.23 |
| 6,363,933 B1 * | 4/2002 | Berthon-Jones | 128/204.23 |
| 6,532,959 B1 | 3/2003 | Berthon-Jones | |
| 6,609,517 B1 | 8/2003 | Estes et al. | |
| 6,675,797 B1 | 1/2004 | Berthon-Jones | |
| 6,739,335 B1 * | 5/2004 | Rapport et al. | 128/204.18 |
| 6,752,151 B2 | 6/2004 | Hill | |
| 6,988,498 B2 | 1/2006 | Berthon-Jones et al. | |
| 7,018,341 B2 | 3/2006 | Wright et al. | |
| 7,640,055 B2 * | 12/2009 | Geva et al. | 600/544 |
| 2002/0124848 A1 * | 9/2002 | Sullivan et al. | 128/204.21 |
| 2003/0023178 A1 * | 1/2003 | Bischoff et al. | 600/515 |
| 2004/0065328 A1 | 4/2004 | Amarasinghe et al. | |
| 2004/0073098 A1 * | 4/2004 | Geva et al. | 600/300 |
| 2006/0084877 A1 * | 4/2006 | Ujhazy et al. | 600/483 |
| 2008/0066753 A1 * | 3/2008 | Martin et al. | 128/204.23 |

OTHER PUBLICATIONS

Hoffstein and Mateika 1994 "cardiac arrhythmias, snoring, and sleep apnea" chest 106(2):466-71.*

Pepperell et al. 2002 "ambulatory blood pressure after therapeutic and subtherapeutic nasal continuous positive airway pressure for obstructive sleep apnoea: a randomized parallel trial" lancet 359(9302:204-10 abstract only.*

Roche et al. 2003 "relationship among the severit of sleep apnea syndrome, cardiac arrhythmias, and autonomic imbalance" pacing clin electrophysiol 26(3): 669-77.*

Chest, Sep. 1999, 116(3):660-666 "Cardiogenic Oscillations on the Airflow Signal During Continuous Positive Airway Pressure as a Marker of Central Apnea" Ayappa et al.

Anesth Analg, Nov.-Dec. 1978, 57(6):647-652 "Automated Measurement and Frequency Analysis of the Pneumocardiogram" Reitan et al.

IEEE Transactions on Biomedical Engineering, vol. BME-28, No. 6, Jun. 1981, pp. 471-475 "The Dynamic Pneumocardiogram: An Application of Coherent Signal Processing to Cardiovascular Measurement".

Notice of Reasons for Rejection, Patent Application No. P2007-500006; Japanese Patent Office, Aug. 17, 2010.

Reitan et al, "Automated measurement and frequency analysis of the Pneumocardiogram", Anesthesia and Analgesia, Williams and Wilkins, Baltimore, MD, US, vol. 57, No. 6, Nov. 1, 1978, pp. 647-652, XP008104309.

Ayappa et al, "Cardiogenic Oscillations on the Airflow Signal During Continuous Positive Airway Pressure as a Marker of Central Apnea", Chest, The College, Chicago, IL, US, vol. 116, No. 3, Sep. 1, 1999, pp. 660-666, XP008104298.

Johnson Walter K, "Dynamic Pneumocardiogram: An Application of Coherent Signal Processing to Cardiovascular Measurement", IEEE Transactions on Biomedical Engineering, IEEE Service Center, Piscataway, NJ, US, vol. BME-28, No. 6, Jun. 1, 1981, pp. 471-475, XP002467749.

* cited by examiner

CARDIAC MONITORING AND THERAPY USING A DEVICE FOR PROVIDING PRESSURE TREATMENT OF SLEEP DISORDERED BREATHING

FIELD OF THE INVENTION

This application claims the priority of U.S. provisional application Ser. No. 60/547,812 filed on Feb. 25, 2004. This invention relates to a method and apparatus for detecting cardiac signals in a CPAP patient's airflow and using the signals to monitor and treat cardiac conditions.

BACKGROUND OF THE INVENTION

Cessation of breathing during sleep for more than 10 seconds is called an "apnea," which leads to decreased blood oxygenation and disruption of sleep. Apneas are traditionally categorized as central, where there is no respiratory effort, or obstructive sleep apnea (OSA), where there is respiratory effort but the airway is blocked. With purely central apneas, the airway is patent (or open), but the patient is not attempting to breathe. With other central apneas and all obstructive apneas, the airway is not patent (i.e., it is occluded). The occlusion is usually at the level of the tongue or soft palate.

The common form of treatment of apneas is the administering of continuous or variable positive airway pressure (referred to herein generally as CPAP). Devices that provide CPAP treatment are described in U.S. Pat. Nos. 5,704,345, 6,532,957, 6,575,163, 6,484,719, 6,688,307, and 6,532,959, incorporated herein by reference. The procedure for administering CPAP treatment has been well documented in both the technical and patent literature. Briefly stated, CPAP treatment acts as a pneumatic splint of the airway by the provision of positive pressure, usually in the range 4-20 cm $H_2O$. The air is supplied to the airway by a motor driven blower whose outlet passes air via a delivery tube or hose to a nose (and/or mouth) mask sealingly engaged to a patient's face. An exhaust port is provided in the delivery tube proximate to the mask. More sophisticated forms of CPAP, such as bi-level CPAP and self-titrating CPAP, are described in U.S. Pat. Nos. 5,148,802 and 5,245,995, respectively.

CPAP therapy is also known to be beneficial to some cardiac pathology, for example, congestive heart failure. By boosting intrathoracic pressure, CPAP offers various (potential) direct benefits in heart failure, for example, impeding venous return (reducing preload), reducing the systolic pressure gradient against which the left ventricle must pump (reduced afterload), and reducing left-ventricular trans-mural pressure (improved contractile efficiency). In addition, CPAP may offer indirect benefits to heart-failure patients, e.g., to counter pulmonary edema, to increase lung volume (may aid ventilatory stability in Cheyne-Stokes respiration), and in patients with a disposition to obstructive apnea, to reduce sympathetic activation through prevention of repetitive OSA.

Various techniques are known for detecting abnormal breathing patterns indicative of obstructed breathing. U.S. Pat. No. 5,245,995, for example, describes how snoring and abnormal breathing patterns can be detected by inspiration and expiration pressure measurements while sleeping, thereby leading to early indication of pre-obstructive episodes or other forms of breathing disorder. Patterns of respiratory parameters are monitored, and CPAP pressure is raised on the detection of pre-defined patterns to provide increased airway pressure to subvert the occurrence of the obstructive episodes and the other forms of breathing disorder.

Central apneas need not involve an obstruction of the airway, and often occur during very light sleep and in patients with various cardiac, cerebrovascular and endocrine conditions unrelated to the state of the upper airway. In cases where the apnea is occurring without obstruction of the airway, there may be little benefit in increasing CPAP pressure, in contrast to an obstructive apnea.

To differentiate between central and obstructed apneas, U.S. Pat. No. 6,029,665, incorporated herein by reference, teaches a CPAP system that monitors pulsatile airflow during the apnea event. With each beat of the heart, of the order of 66 ml of blood is ejected from the chest over about 0.3 sec, producing a pulsatile blood flow out of the chest of the order of 0.22 l/sec peak flow. If the chest wall were rigid this would create a partial vacuum in the chest cavity, and, if the upper airway were open and had zero flow resistance, a similar quantity of air would be sucked in through the trachea. In practice, the chest wall is not totally rigid, and the airways have finite airflow resistance. Consequently the measurable airflow (or cardiogenic oscillation) with each beat of the heart is of the order of 0.02 to 0.1 l/sec.

If there is a central apnea with an open airway, the device of the '665 patent will sense cardiogenic oscillations in the air pressure, and determine that an unobstructed central apnea event has occurred. Conversely, if the airway is closed, the pressure waveform will not have any noticeable cardiogenic oscillations, and the device of the '665 patent will determine that the apnea event was an obstructed event.

Implementing the apparatus and method of the '665 patent prevents the inappropriate increase in the splinting CPAP air pressure during a central apnea, thereby preventing an unnecessary increase in pressure that may otherwise reflexively inhibit breathing and further aggravate the breathing disorder. The device is also used in a diagnostic mode, using nasal cannulae in the place of a face mask, where measurements of apneas, patency, and partial obstruction are logged, but no CPAP treatment is effected. The data provides a physician with the ability to diagnose conditions such as OSA and upper airway resistance syndrome.

Neither the '665 patent nor other prior art utilizes measurements of cardiogenic oscillations in a CPAP patient's airflow for monitoring or treating conditions related to cardiac health.

OBJECTS AND SUMMARY OF THE INVENTION

It is an object of the invention to utilize a CPAP device that treats sleep disordered breathing (SDB) also as a cardiac treatment device by monitoring cardiac signals in a patient's airflow to determine cardiac health.

More specifically, it is an object of the invention to monitor the cardiac signals to screen and diagnose cardiac morbidity conditions, such as the existence of arrhythmias, and to influence and optimize cardiac stroke volume.

It is a further object to monitor pulse-transit time, changes in the heart pre-ejection period, and the duration of the cardiac cycle.

To satisfy the recited objectives, a method is disclosed of sensing cardiogenic oscillations in a patient's airflow and monitoring the patient's cardiac condition from the cardiogenic oscillations. The apparatus diagnoses cardiac morbidity conditions, such as the existence of arrhythmias or other cardiac abnormalities and influences and optimizes cardiac stroke volume. The apparatus further monitors pulse-transit time, changes in the heart pre-ejection period, and the duration of the cardiac cycle.

BRIEF DESCRIPTION OF THE FIGURES

To further satisfy the recited objectives, a detailed description of typical embodiments of the invention is provided with reference to appended drawings that are not intended to limit the scope of the invention, in which.

DESCRIPTION OF THE INVENTION

Figure 1:
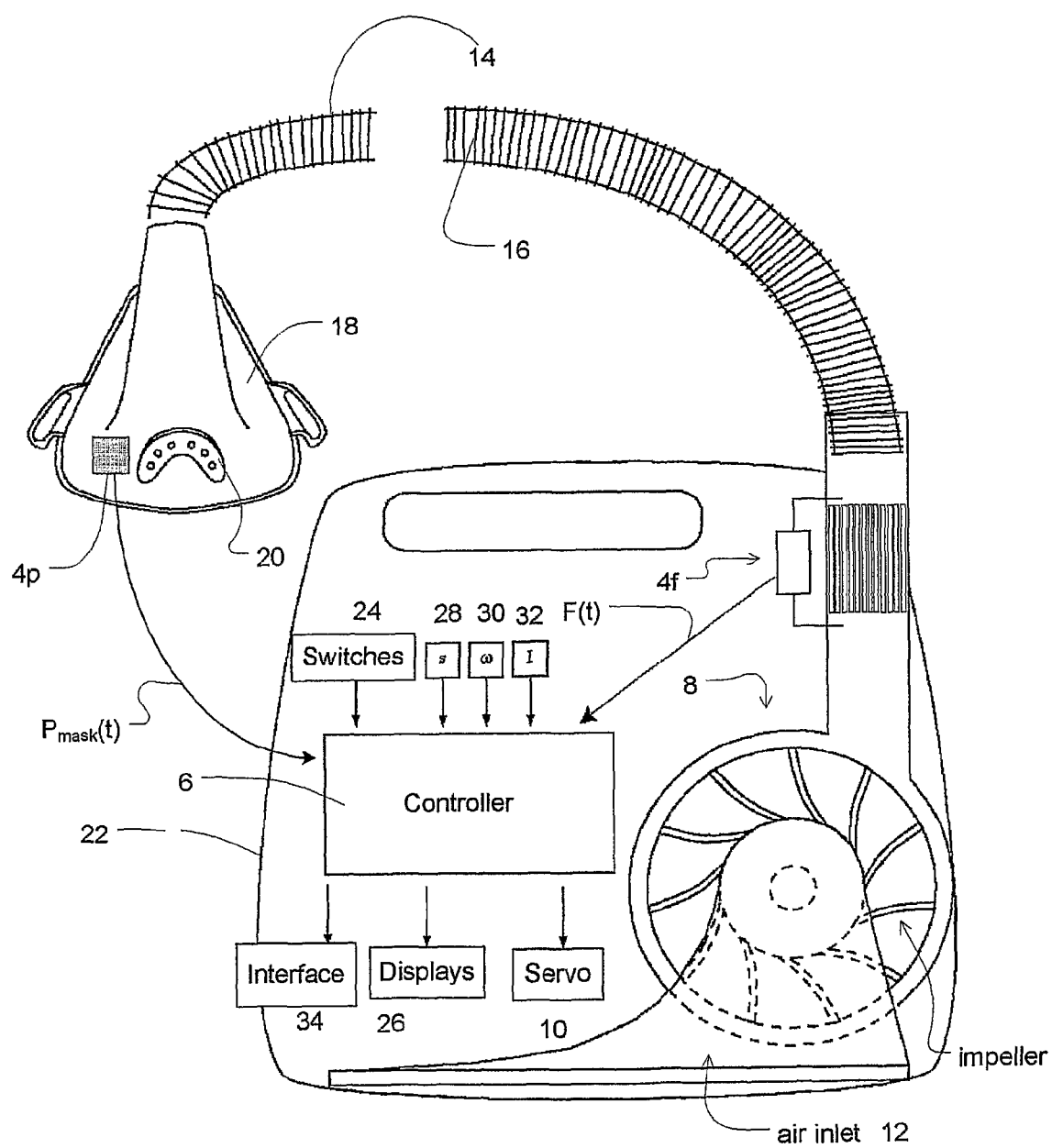
FIG. 1 is a diagram of an apparatus that treats sleep disordered breathing during sleep and monitors cardiac signals in a CPAP patient's airflow to assess cardiac health and treat cardiac conditions.

Turning to FIG. 1, a device for treating SDB during sleep is disclosed that is capable of carrying out the features of the invention (such as a CPAP device), including sensing cardiogenic oscillations in air pressure/flow readings to determine whether an apnea event is central or obstructed. Mask flow is measured using a flow sensor 4f and/or pressure sensor 4p with a pneumotachograph and differential pressure transducer or similar device. A flow signal F(t) is derived and mask pressure is measured at a pressure tap using a pressure transducer to derive a pressure signal $P_{mask}(t)$. The pressure sensor 4p and flow sensor 4f have been shown only symbolically in FIG. 1 since those skilled in the art would understand how to measure flow and pressure.

Flow F(t) and pressure $P_{mask}(t)$ signals are sent to a controller or microprocessor 6 which then determines how to adjust the blower. The controller 6 may include integrated circuits, a memory and/or other instruction or data storage medium. Programmed instructions with control methodology may be coded on integrated chips in the memory of the device (e.g., firmware) or loaded as software.

The pressure delivery device includes a blower 8, which preferably is an impellor. The impellor 8 is controlled by a servo 10, receives ambient air through an inlet 12 and delivers pressurized air through an outlet 14 defined by an air delivery conduit 16 and a mask 18 with an integrated exhaust vent 20. The impellor, motor, and controller assembly define a blower assembly and are located within the blower housing 22. Various switches 24 and displays 26 are provided in the blower housing. A number of sensors are provided within the blower to monitor, among other things, snore 28, motor speed 30, and motor current 32. Various devices known in the art can serve as these types of sensors. A communication interface 34 allows data to be transferred between the apparatus and an external device, such as a computer or controller.

If cardiogenic oscillations are not reflected in the pressure in a patient's mask during an apnea event, then the patient may be experiencing an obstructed central apnea event or an obstructed apnea event with respiratory effort. The above measuring technique, by itself, is incapable of differentiating the two conditions so that an indicator of respiratory effort is required. One type of known detector detects when the skin in the suprasternal notch is sucked inwards (during inhalation) and when the skin bulges outward (during expiratory efforts). Such a device is taught in U.S. Pat. No. 6,445,942, incorporated herein by reference, which can be used to identify the occurrence of a central apnea.

Figure 2:
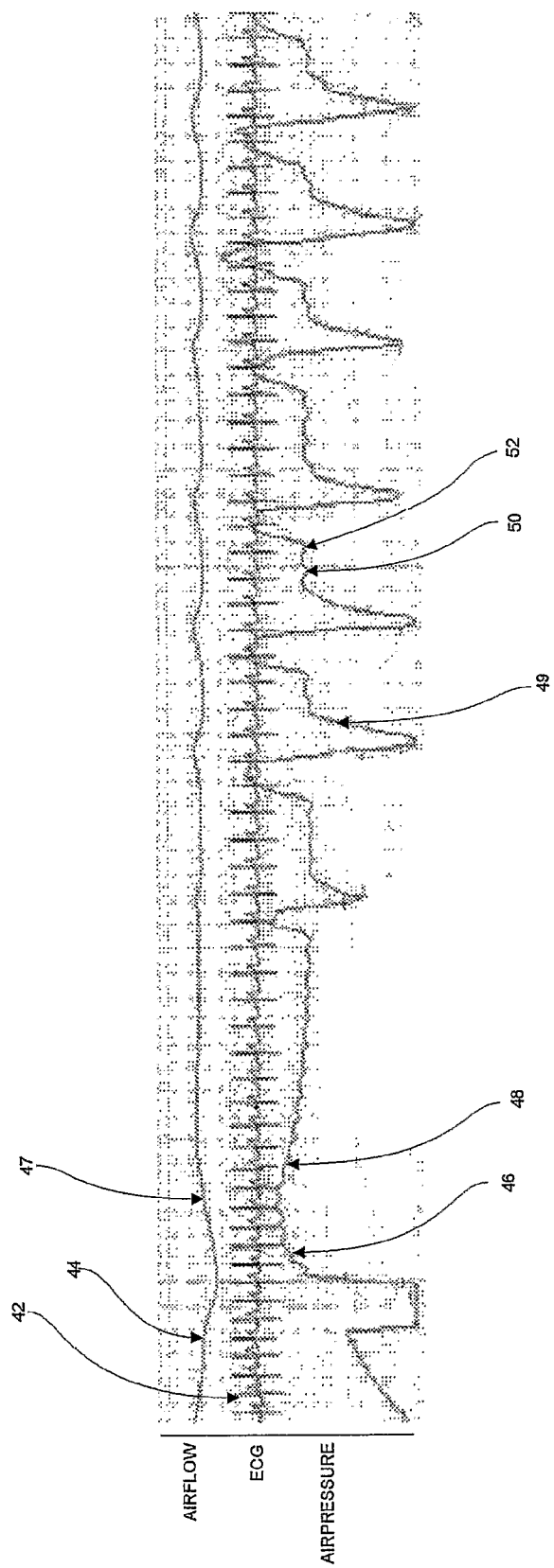
FIG. 2 is a graph illustrating, over a selected time period, airflow, ECG and mask air pressure.

FIG. 2 illustrates traces that may be recorded by appropriate equipment. Trace 42 illustrates a patient's electrocardiogram (ECG), trace 44 is the CPAP patient's airflow and trace 46 is the patient's air pressure as measured using the CPAP treatment device. (Either or both of airflow and pressure may be monitored.) In the vicinity of numeral 47, the respiratory flow hovers around zero, indicating an apnea event. The air pressure trace 46 still exhibits cardiogenic oscillations 48 indicative of an open airway (unobstructed) central apnea event.

When monitoring air pressure 46, a band filter may be used. A suitable filter rejects signals of 30 Hz or lower (i.e., rejects those signals which are generally associated with respiration and physical movement of the patient) and also rejects signals higher than 60 Hz (i.e., reject those signals which are generally associated with system noise rather than being representative of cardiogenic events).

Once cardiogenic information is in hand, it can be used to better manage conventional triggering circuits for a bi-level CPAP ventilator (which typically adjust the ventilator in response to inspiratory and expiratory flow), since distortions of air flow measurements attributable to cardiogenic oscillations can be ignored. Of particular interest is the identification and filtering out of cardiogenic flow oscillation occurring at the end-expiration (i.e., cardiogenic oscillation signals occurring at a part of the respiratory phase when it is desirable for the ventilator to most accurately cycle from expiration to inspiration in accordance with the applicable treatment algorithm).

Studying the presence of cardiogenic oscillations and, if present, their amplitude and frequency, during an open apnea event over a period of several seconds, without the complication of the concurrent existence of the airflow signal, provides information concerning the patient's cardiac condition. A medical practitioner can assess the patient's cardiac condition and treatment needs given the known association of central apneas and cardiac morbidity.

While the cardiogenic airflow may be detected during any portion of the patient's respiratory cycle, the best resolution of the cardiogenic oscillations 48 occurs during the middle to end of the expiration portion 49 of the patient's breath. Monitoring the signal in only this relatively small window simplifies the processing needed to achieve the requisite signal resolution. Indeed, for some applications, it may be sufficient to monitor cardiogenic oscillations during only that portion of the respiratory cycle, i.e., significantly less than all the heartbeats per breath.

To locate the middle to end of the expiratory cycle, the controller detects the start of a new expiration cycle (with a threshold detector that detects the zero line transition), and identifies the end of the exhalation based on the recent averaged lapsed time of breathing cycles. Alternatively, the later portion of exhalation may be isolated using continuous phase monitoring of the patient's breathing, as disclosed in the '957 patent referenced above.

Through long term monitoring of the cardiogenic oscillations 48, irregularities in the force or rhythm of the heartbeat signal can be detected, which enables the determination of an arrhythmia. The amplitude and/or frequency of the signal may be compared to thresholds representing expected or prior average heartbeat force and/or rhythm for the patient to determine any deviation from a norm. Similarly, other patterns indicative of arrhythmia or normal cardiac force/rhythm may be stored as templates and compared to the signal to detect the presence of an arrhythmia or the absence of normal cardiac functioning.

If an arrhythmia is detected, then the device may send a signal to the patient, care provider or physician, or record the event for later observation. The signal to the patient may be in the form of an audible alarm. The signal to the care provider or physician may be in the form of an automated text messaging system using known telephonic circuitry and a subscription to a cellular provider. Immediate action and treatment is therefore enabled which is particularly useful in view of the known co-morbidity involving cardiac conditions and respiratory disorders such as SDB.

The determination of cardiac timing is possible by monitoring the average time between cardiogenic oscillations such as 50 and 52. From this timing, heart rate parameters can be deduced such as average rate, variability and arrhythmia. All information regarding cardiac conditions may be observed in real time by way of suitable display, transmitted or recorded. Ventilatory support may be modified so as to assist cardiac function where, for example, CPAP therapy pressure is changed according to the cardiac cycle to assist right atria filling (pressure decrease), left ventricular ejection (pressure increase), and cardiac perfusion (pressure increase at early diastole), etc.

It has been observed that cardiac stroke volume affects the amplitude of cardiogenic oscillations and that CPAP treatment affects stroke volume. Therefore, by monitoring cardiogenic oscillations in accordance with the present invention, it is possible to titrate CPAP treatment so as to influence and preferably to optimize cardiac stroke volume. This may be achieved without uninterrupted monitoring of heartbeats. Rather it may be achieved with the monitoring of only 1-2 heartbeats per breath, i.e., by monitoring only during a portion of the respiratory cycle, preferably during the middle to end expiration portion. For example, stroke volume may be maximized by examining the amplitude of the cardiogenic oscillations and servo-controlling the pressure treatment accordingly.

It has been proposed that pulse-transit time (PTT) may serve as a non-invasive means of inferring respiratory effort and arousals. The PTT is the time in which a pulse wave propagates the length of an arterial tree and is measured by the time interval that starts when half of the ventricular myocardium has been depolarized and ends when the blood is saturated with a predetermined percentage (depending on the age and condition of the patient) of oxyhemoglobin ($SpO_2$). The former occurs when an R-wave is sensed in the ECG QRS complex (the entire time it takes for depolarization of the ventricles), and the latter occurs when a typical finger pulse oximeter senses photoplethysmographic (pulse) waveforms.

The disadvantage of the typical measurements of the PPT is that the pre-ejection period (PEP) is included in the measured delay. The present invention allows for the achievement of a more accurate measure of pulse-transit time (i.e., a measure of pulse-transit time without the pre-ejection period component). By performing uninterrupted monitoring of cardiogenic oscillations concurrently with pulse oximetry, PTT may be estimated. An advantage of the present invention is that it uses cardiogenic oscillations for measuring cardiac timing. The cardiogenic oscillations relate to the heart's mechanical systolic events rather than the electrical systolic events, so the PEP is not included.

Changes in the heart's PEP can also be assessed by the concurrent monitoring of cardiogenic oscillations against the ECG trace 42, and following the lag in time between electrical and mechanical systolic events. The changes in the PEP reflect the ability of the left ventricle to eject (perform mechanical systole events) and are another indication of cardiac health, and blood pressure, as well as peripheral vascular resistance and other cardio-circulatory conditions of interest in patient management.

In summary, the apparatus may be configured or programmed to do the following while the patient is wearing a mask: measure airflow; identify and isolate the cardiogenic signal from the airflow; identify central apneas; calculate heart rate from the cardiogenic signal; determine abnormalities in heart rate (e.g., arrhythmias); generate notifications if an abnormality is determined, where the notifications include an alarm or other means of contacting selected individuals; monitor cardiac timing and assist in cardiac function; more accurately determine respiratory effort; and monitor PTT and PEP.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

What is claimed is:

1. A continuous positive airway pressure (CPAP) apparatus for providing CPAP therapy, the apparatus comprising:
    a pressure sensor for generating a pressure signal indicative of a mask pressure; and
    a controller configured to:
        receive the pressure signal generated by the pressure sensor;
        identify cardiogenic pressure oscillations in the pressure signal;
        determine an attribute of the cardiogenic pressure oscillations;
        derive a heart rate parameter from the determined attribute of the cardiogenic pressure oscillations; and
        assess the heart rate parameter to determine the patient's cardiac condition.

2. The apparatus of claim 1 wherein the controller:
    identifies a central apnea event by determining the occurrence of cardiogenic oscillations during a period of no airflow; and
    determines the patient's cardiac condition based upon the known association of central apneas and cardiac morbidity.

3. The apparatus of claim 1 wherein the controller uses cardiogenic oscillations in only the middle to later portion of exhalation to determine the patient's cardiac condition.

4. The apparatus of claim 3 wherein the controller determines the middle to later portion of exhalation by tracking the recent averaged lapsed time of prior breathing cycles and using such time in conjunction with the detection of the start of a breathing cycle.

5. The apparatus of claim 1 wherein the controller identifies an arrhythmia event by:
    monitoring the cardiogenic oscillations over a long-term period of time;
    detecting irregularities in the force or rhythm of a heartbeat signal through the monitoring;
    comparing an amplitude or frequency of the heartbeat signal to a threshold indicative of norm to determine a deviation; and
    determining the presence of an arrhythmia event based on the deviation.

6. The apparatus of claim 1 wherein the controller determines cardiac timing from the time between cardiogenic oscillations.

7. The apparatus of claim 1 wherein the controller is further configured to change a control parameter in response to the determined patient's cardiac condition.

8. The apparatus of claim 7 wherein the control parameter is pressure.

9. The apparatus of claim 1 wherein the controller measures pulse transit time by monitoring cardiogenic oscillations concurrently with pulse oximetry.

10. The apparatus of claim 1 wherein the controller determines changes in the patient's pre-ejection period by analyzing the cardiogenic oscillations against concurrent electrocardiogram (ECG) waveforms.

11. The apparatus of claim 1 wherein the controller uses cardiogenic oscillation information for managing triggering of the CPAP apparatus.

12. The apparatus of claim 1, further comprising a flow sensor to generate a flow signal.

13. The apparatus of claim 1, wherein the attribute of the cardiogenic pressure oscillations includes an amplitude, frequency of the cardiogenic pressure oscillations, or an average time between cardiogenic oscillations.

14. The apparatus of claim 1, wherein the heart rate parameter includes a force, rhythm, amplitude, frequency, average rate, or variability of a heartbeat.

15. A continuous positive airway pressure (CPAP) apparatus for providing CPAP therapy, the apparatus comprising:
    a pressure sensor for generating a pressure signal indicative of a mask pressure; and
    a controller configured to:
        receive the pressure signal generated by the pressure sensor;
        identify cardiogenic pressure oscillations in the pressure signal;
        determine an attribute of the cardiogenic pressure oscillations;
        derive a heart rate parameter from the determined attribute of the cardiogenic pressure oscillations;
        assess the heart rate parameter to determine the patient's cardiac condition; and
    change a control parameter in response to the determined cardiac condition.

16. The apparatus of claim 15 wherein the controller:
    identifies the occurrence of a central apnea event by determining the occurrence of cardiogenic oscillations during a period of no airflow; and
    determines the patient's cardiac condition based upon the known association of central apneas and cardiac morbidity.

17. The apparatus of claim 15 wherein the controller uses cardiogenic oscillations in only the middle to later portion of exhalation to determine the patient's cardiac condition.

18. The apparatus of claim 17 wherein the controller determines the middle to later portion of exhalation by tracking the recent averaged lapsed time of prior breathing cycles and using such time in conjunction with the detection of the start of a breathing cycle.

19. The apparatus of claim 15 wherein the controller identifies an arrhythmia event by:
    monitoring the cardiogenic oscillations over a long-term period of time;
    detecting irregularities in the force or rhythm of a heartbeat signal through the monitoring;
    comparing an amplitude or frequency of the heartbeat signal to a threshold indicative of norm to determine a deviation; and
    determining the presence of an arrhythmia event based on the deviation.

20. The apparatus of claim 15 wherein the controller determines cardiac timing from the time between cardiogenic oscillations.

21. The apparatus of claim 15 wherein the control parameter is pressure.

22. The apparatus of claim 15 wherein the controller measures pulse transit time by monitoring cardiogenic oscillations concurrently with pulse oximetry.

23. The apparatus of claim 15 wherein the controller determines changes in the patient's pre-ejection period by analyzing the cardiogenic oscillations against concurrent electrocardiogram (ECG) waveforms.

24. The apparatus of claim 15 wherein the controller uses cardiogenic oscillation information for managing triggering of a bi-level CPAP apparatus.

25. The apparatus of claim 15, further comprising a flow sensor to generate a flow signal.

26. The apparatus of claim 15, wherein the attribute of the cardiogenic pressure oscillations includes an amplitude, frequency of the cardiogenic pressure oscillations, or an average time between cardiogenic oscillations.

27. The apparatus of claim 15, wherein the heart rate parameter includes a force, rhythm, amplitude, frequency, average rate, or variability of a heartbeat.

28. A method of determining a patient's cardiac condition by using a CPAP apparatus of claim 1 for treating sleep disordered breathing, comprising the steps of:
    sensing the patient's cardiogenic pressure or flow oscillations; and
    using the sensed cardiogenic oscillations to determine the patient's cardiac condition.

29. The method of claim 28 wherein the occurrence of a central apnea event is identified by determining the occurrence of cardiogenic oscillations during a period of no airflow and wherein the patient's cardiac condition is determined based upon the known association of central apneas and cardiac morbidity.

30. The method of claim 28 wherein cardiogenic oscillations in only the middle to later portion of exhalation are used to determine the patient's cardiac condition.

31. The method of claim 30 wherein the middle to later portion of exhalation is determined by tracking the recent averaged lapsed time of prior breathing cycles and using such time in conjunction with the detection of the start of a breathing cycle.

32. The method of claim 28 further comprising the step of sending a signal to the patient, care provider or physician, or recording an arrhythmia event for later observation, upon determining the existence of an arrhythmia event.

33. The method of claim 28 further comprising the step of determining cardiac timing from the time between cardiogenic oscillations.

34. The method of claim 28 further comprising the step of adjusting the patient's stroke volume by examining the amplitude of the cardiogenic oscillations and in accordance therewith adjusting the CPAP treatment pressure.

35. The method of claim 28 further comprising the step of analyzing the cardiogenic oscillations to determine the patient's pulse transit time.

36. The method of claim 28 further comprising the step of analyzing the cardiogenic oscillations against ECG waveforms to determine changes in the patient's pre-ejection period.

37. The method of claim 28 further comprising the step of assisting cardiac function in accordance with the determined cardiac condition by adjusting the CPAP treatment pressure to assist right atria filling, left ventricular ejection, or cardiac perfusion.

38. The method of claim 28 further comprising the step of assisting cardiac function by adjusting the CPAP treatment pressure to assist right atria filling, left ventricular ejection, cardiac perfusion, or arterial tone.

39. The method of claim 28 further comprising the step of using cardiogenic oscillation information for managing triggering of a bi-level CPAP apparatus.

40. A method of determining a patient's cardiac condition and providing cardiac treatment by using a CPAP apparatus of claim 1 for treating sleep disordered breathing, comprising the steps of:
sensing the patient's cardiogenic pressure or flow oscillations; and
using the sensed cardiogenic oscillations to determine the patient's cardiac condition and adjust the pressure delivered by the CPAP apparatus to treat the patient's cardiac condition.

41. The method of claim 40 wherein the occurrence of a central apnea event is identified by determining the occurrence of cardiogenic oscillations during a period of no airflow and wherein the patient's cardiac condition is determined based upon the known association of central apneas and cardiac morbidity.

42. The method of claim 40 wherein cardiogenic oscillations in only the middle to later portion of exhalation are used to determine the patient's cardiac condition.

43. The method of claim 42 wherein the middle to later portion of exhalation is determined by tracking the recent averaged lapsed time of prior breathing cycles and using such time in conjunction with the detection of the start of a breathing cycle.

44. The method of claim 40 further comprising the step of sending a signal to the patient, care provider or physician, or recording an arrhythmia event for later observation, upon determining the existence of an arrhythmia event.

45. The method of claim 40 further comprising the step of determining cardiac timing from the time between cardiogenic oscillations.

46. The method of claim 40 further comprising the step of adjusting the patient's stroke volume by examining the amplitude of the cardiogenic oscillations and in accordance therewith adjusting the CPAP treatment pressure.

47. The method of claim 40 further comprising the step of analyzing the cardiogenic oscillations to determine the patient's pulse transit time.

48. The method of claim 40 further comprising the step of analyzing the cardiogenic oscillations against ECG waveforms to determine changes in the patient's pre-ejection period.

49. The method of claim 40 further comprising the step of assisting cardiac function in accordance with the determined cardiac condition by adjusting the CPAP treatment pressure to assist right atria filling, left ventricular ejection, or cardiac perfusion.

50. The method of claim 40 further comprising the step of assisting cardiac function by adjusting the CPAP treatment pressure to assist right atria filling, left ventricular ejection, or cardiac perfusion.

51. The method of claim 40 further comprising the step of using cardiogenic oscillation information for managing triggering of a bi-level CPAP apparatus.

\* \* \* \* \*